United States Patent [19]

Dali et al.

[11] 4,280,505
[45] Jul. 28, 1981

[54] FIXATION RING FOR TRANSCUTANEOUS GAS SENSOR PROBE

[75] Inventors: Carmelo Dali, Chesire; David R. Rich, E. Hartford, both of Conn.

[73] Assignee: Novametrix Medical Systems, Inc., Wallingford, Conn.

[21] Appl. No.: 50,200

[22] Filed: Jun. 20, 1979

[51] Int. Cl.³ .............................................. A61B 5/00
[52] U.S. Cl. ............................ 128/635; 204/195 B; 204/195 P
[58] Field of Search ................. 128/635, 632, 641; 204/195 B, 195 P, 195 M

[56] References Cited

U.S. PATENT DOCUMENTS

| | | | |
|---|---|---|---|
| 3,659,586 | 5/1972 | Johns et al. | 128/635 |
| 3,795,239 | 3/1974 | Eberhard et al. | 204/195 B X |
| 3,835,014 | 9/1974 | Huffhines, Jr. | 204/195 P |
| 3,838,034 | 9/1974 | Groves | 204/195 P X |
| 3,942,517 | 3/1976 | Bowles et al. | 128/641 |
| 4,185,620 | 1/1980 | Hagihara | 128/635 |
| 4,197,853 | 4/1980 | Parker | 128/635 |

FOREIGN PATENT DOCUMENTS

| | | | |
|---|---|---|---|
| 2724461 | 12/1977 | Fed. Rep. of Germany | 128/635 |
| 2003275 | 3/1979 | United Kingdom | 128/635 |

OTHER PUBLICATIONS

Scacci et al., "O₂ Tension Monitoring," Med. Inst., vol. 10, No. 4, pp. 192–194, Jul.–Aug. 1976.
Vesterager, "Transcutaneous $PO_2$ Electrode," Scand. J. Clin. Lab. Invest., 37 (Supp. 146), 27–30, 1977.

*Primary Examiner*—Lee S. Cohen
*Attorney, Agent, or Firm*—Howard F. Mandelbaum

[57] ABSTRACT

A fixation ring for a transcutaneous gas sensor probe adapted to be removably mounted on the probe with a bore in the ring communicating with the electrodes of the probe. The fixation ring includes a membrane mounted therein which is tensioned in cooperation with the probe when the fixation ring is attached to the probe at which time the membrane permits only gases to which it is permeable to pass through the bore in the fixation ring and into an ion solution in contact with the electrodes of the probe. A cap member removably mountable on the fixation ring is provided with a resilient disc for depressing the membrane to prevent excessive ion solution and any entrapped air from accumulating adjacent to the electrodes.

15 Claims, 3 Drawing Figures

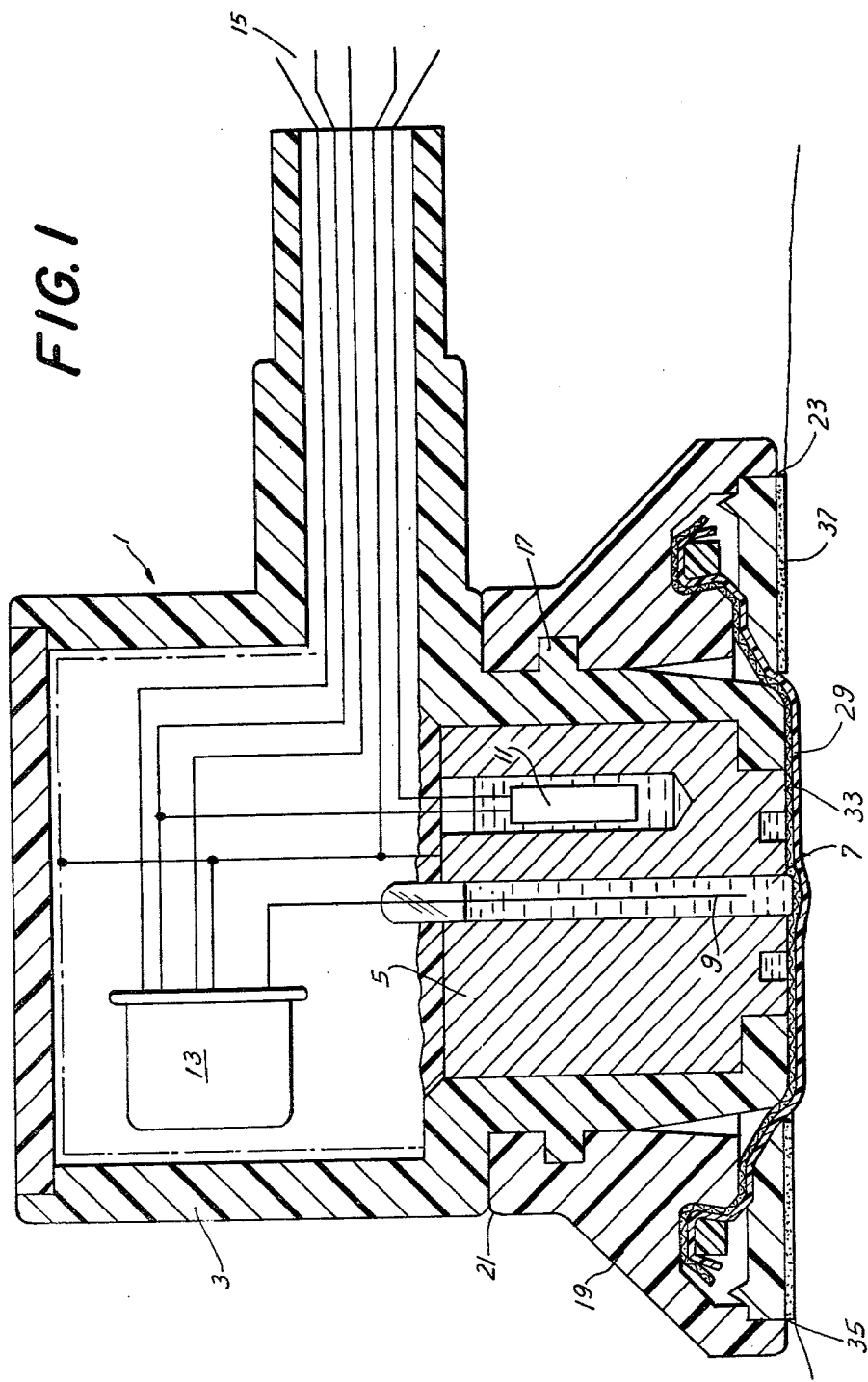

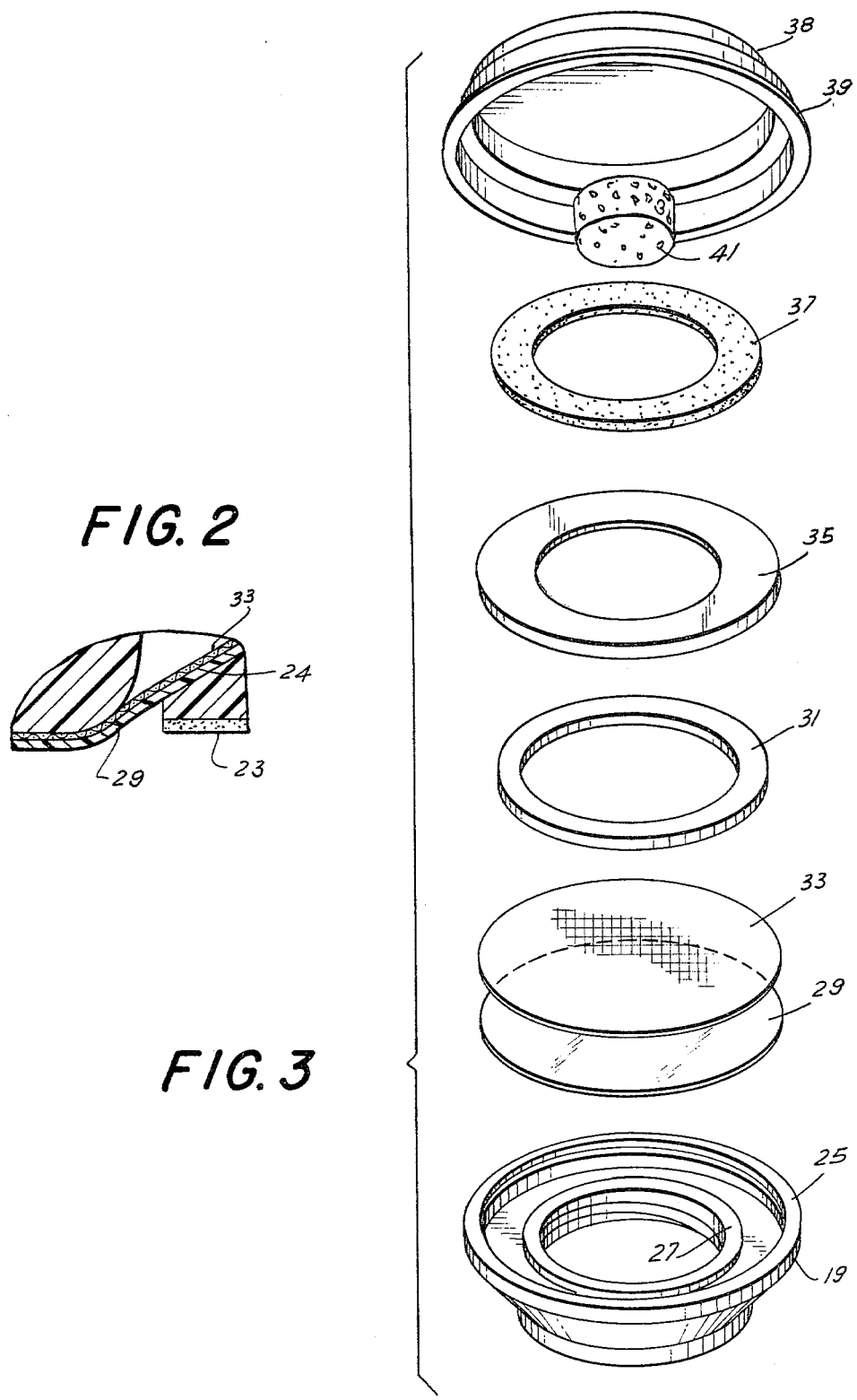

FIXATION RING FOR TRANSCUTANEOUS GAS SENSOR PROBE

BACKGROUND OF THE INVENTION

This invention relates to transcutaneous gas sensor probes used for the measurement of transcutaneous gases emitted through the skin of a living body. More specifically, the invention concerns a fixation ring upon which a membrane permeable to the gas to be measured but impermeable to an ion solution can be premounted and packaged under clean conditions to be later connected to the active portion of a transcutaneous gas sensor probe without need for special handling, instruments or skill.

It is known in the medical art of non-invasive blood gas content monitoring and measurement to apply to the surface of the skin of a person whose blood gas content is to be monitored and measured, a probe having a barrier permeable to the gas to be measured or monitored and impermeable to other gases as well as to an ion solution in which the gas which is to be monitored and measured is soluble. Such probes generally include a first electrode or anode, a second electrode or cathode, an ion solution in contact with the anode and cathode and a membrane spanning a region between the anode and cathode and maintaining a supply of the ion solution in contact with the anode and cathode. A particular gas which is emitted from the skin of a living body is permitted to permeate through the membrane and into the ion solution where it has an effect on the flow of current between the cathode and anode for permitting an electrical measurement indicative of the quantity of the gas emitted from the skin.

In the use of conventional transcutaneous gas probes, membranes are attached to the probes by the physician or technician applying each probe before its application. This requires difficult handling by highly skilled personnel who must use special tools to install the membranes with a fastener, such as an O-ring. Such preparation is required with each use of the probe. The membranes are small, light, susceptible to damage from improper handling, and generally difficult to install in a transcutaneous gas probe. Once installed, the membranes are likely to shift relative to the electrodes, thereby resulting in displacement of the electrolyte and upsetting the calibration, sensitivity and stability of the probe. Also, the difficulty in changing the membranes on prior art probes encourages the repeated use of membranes which should be changed after each use thereby creating unsanitary conditions.

It is known in the prior art to employ a separate attachment ring with a transcutaneous gas sensor probe which attachment ring can be attached to the skin of a patient and which is adapted to receive the active part of the probe. Such attachment rings are beneficial in that they obviate the need to sterilize the probe between patient uses. Since only the attachment ring is brought into contact with the skin of the patient, only it need be sterilized between uses. Such attachment rings can also be provided with adhesive coatings on their surfaces adapted to engage the skin of the body for securing a transcutaneous gas sensor probe in place on the surface of the skin. A transcutaneous gas sensor probe having a removable attachment ring with an adhesive coating is disclosed in German Pat. No. 27 24 461, issued to Radiometer A/S of Copenhagen, Denmark, for a sensor for transcutaneous electrochemical measurements. Although the probe disclosed in the German patent obviates the need for sterilizing the entire probe with each use and provides a positive method of affixing the probe to the skin surface of a patient, it does not solve the above described problem of attaching the membrane to the probe without the performance of a relatively difficult operation. Moreover, prior art probes do not provide for a sufficiently positive engagement of the membrane by the sensor to prevent substantial movement between the membrane and electrodes which can degrade measurement readings and necessitate recalibration of the probe.

SUMMARY OF THE INVENTION

The present invention overcomes the problems of the prior art in providing a transcutaneous gas sensor probe having a removable fixation ring to which the probe membrane can be affixed prior to application of the fixation ring to the sensor probe. Specifically, the present invention teaches the construction and use of a fixation ring adapted to be mounted on a transcutaneous gas sensor probe having a cathode and anode and ion solution in contact with the cathode and anode. The fixation ring has mounted within it a membrane for maintaining the solution in engagement with the cathode and anode and permitting a gas to be measured to permeate into the ion solution. The fixation ring further includes a housing having a probe end and a body end with a bore running from the probe end to the body end of the housing, means for removably mounting the fixation ring on the probe with the probe end of the fixation ring in engagement with the probe, and means for mounting the membrane on the fixation ring proximate the body end and in sealing relationship with the bore so that only a gas to which the membrane is permeable can pass through the bore from the body skin surface at which it is emitted and into the sensor probe. The invention provides for the mounting of a cover ring on the fixation ring which helps compress the periphery of the membrane to tension it and provides a skin engaging surface which can optionally be provided with an adhesive coating for adherence to the skin. The fixation ring is dimensioned so that the body end of the probe, which is urged against the membrane when the fixation ring is attached to the probe extends slightly beyond the cover member thereby tensioning the membrane against the holding force of the cover ring to limit movement of the membrane with respect to the probe and thus ensure the precision and accuracy of transcutaneous gas measurements. A cap member can be removably attached to the fixation ring for protecting the membrane prior to use, and resiliently urging the membrane toward the electrodes to bleed any entrapped air from the system and displace excess electrolyte between the membrane and the electrodes, and to cause the membrane to conform to the profile of the electrode surfaces thereby further enhancing gas measurements.

Other and further objects of the invention will be apparent from the following drawings and description of a preferred embodiment of the invention in which like reference numerals are used to indicate like parts in the various views.

DESCRIPTION OF THE DRAWINGS

FIG. 1 is a sectional elevation of a fixation ring, embodying the invention in its intended environment.

FIG. 2 is an enlarged fragmentary sectional elevation of a portion of the preferred embodiment of the invention in its intended environment.

FIG. 3 is an exploded perspective view of the apparatus of the preferred embodiment of the invention.

DESCRIPTION OF THE PREFERRED EMBODIMENT

Referring now to FIG. 1 of the drawings, there is shown a transcutaneous gas sensor probe 1, including a housing 3 in which there is mounted an anode 5 formed from a solid billet of a conductive material such as silver and a cathode 7, which for purposes of illustration is shown to be a hollow cylindrical glass tube partially filled with an electrolyte solution in which there is suspended a silver-silver chloride wire electrode 9. Such electrodes are known for use in measuring carbon dioxide gas emitted through the skin of a living body. However, it is to be appreciated that the present invention is not to be limited to use with probes for measuring carbon dioxide and will have application with probes used for measurement of other transcutaneous gases such as oxygen. In the case of an oxygen probe, for example, the cathode may differ from the one shown in FIG. 1 and will often include a plantinum wire mounted within a solid glass rod with the end of the wire substantially coextensive with the end of the rod.

Also shown mounted within the transcutaneous gas sensor probe of FIG. 1 is a temperature sensitive element 11 which can be a thermistor or a field effect transistor for generating a signal indicative of the temperature of the anode 5. The anode 5, cathode 7 and thermistor 11 are connected to electronic circuitry for processing and amplification, part of which can be housed in a module 13 within the housing of the probe, and are connected by wires 15 extending from the probe housing 3 to external processing circuitry and monitoring devices.

The housing 3 has a cylindrical upper portion of enlarged diameter forming a grasping end at which the probe 1 can be conveniently held and a lower cylindrical body portion of lesser diameter terminating in a body end adapted to be urged against the skin of a living body. On the exterior wall of the lower cylindrical body portion, there are provided threads 17 adapted to mate with corresponding threads in the interior bore of a housing 19 of a removable fixation ring. The fixation ring has a probe end 21 which engages the shoulder formed at the juncture of the enlarged diameter and lesser diameter portions of the probe housing 3 when the fixation ring is fully threaded on the housing 3 and a body end 23 adapted to be urged towards the skin of the body of a patient when the probe 1 is applied for transcutaneous gas measurement. The second housing 19, that is the housing of the fixation ring, has a circular bore running its full length from the probe end 21 to the body end 23 of the fixation ring. The bore of the housing 19 tapers slightly outwardly toward the body end while the outer circumference of the lesser diameter portion of the first or probe housing 3 tapers slightly inwardly toward its body end, thereby leaving a void between the outer wall of the housing 3 and the adjacent inner wall of the fixation ring housing 19.

As can be seen with the additional aid of FIG. 3, the fixation ring housing 19 has axially directed outer and inner circumferential ridges 25 and 27 respectively. The inner circumferential ridge 27 of the fixation ring housing 19 is adapted to support the overlapping periphery of a selectively permeable seal including a membrane 29 which can be affixed to the inner ridge 27 by means of a resiliently expandable O-ring or snap-ring 31. The snap-ring 31 can be forced over the peripheral surface region of the membrane 29 and onto the outer circumference of the inner ridge 27 to affix the membrane 29 to the housing 19 in a tensioned state thereby sealing the bore at the body end of the housing 19. The membrane 29, when so affixed, prevents substantially all matter, except that to which the membrane 29 is permeable, from passing into the bore in the housing 19 and entering an ion solution which is maintained within the probe 1 in contact with the anode 5 and cathode 7 by the ion permeable membrane 29.

The membrane 29 is selected according to the transcutaneous gas which is to be measured. For example, if the gas is oxygen, a polypropylene material may be used for the membrane 29, whereas if the transcutaneous gas is carbon dioxide, a teflon membrane may be used. In order to control the amount of ion solution at the measuring surface at the cathode 7, the selectively permeable seal can include an absorbant spacer element 33 disposed between the membrane 29 and the probe end of the fixation ring housing 19. The spacer element 33 is preferably formed from an absorbant material, such as cellulose. The element 33 absorbs the ion solution above the membrane 29 and provides a controlled amount of the solution, which is dependent upon the dimensions and absorbancy of the spacer 33, between the anode 5 and cathode 7 so that accurate and precise gas measurements can be made. The spacer element 33 and membrane 29 are mounted together on the ridge 27 by means of the snap-ring 31 with their adjacent surfaces in intimate contact.

The snap-ring 31 holds both the membrane 29 and spacer 33 securely on the fixation ring 19 by compressing the respective edges of the membrane 29 and spacer 33 against the interior ridge 27 of the housing 19. The exterior wall of the interior ridge 27 is frustoconical and slopes radially inwardly in a direction from the body end to the probe end of the fixation ring housing 19. The sloping wall prevents the snap-ring 31 from becoming dislodged from the ridge 27 once it is forced onto the ridge and into position to hold the membrane 29 and spacer 33 in place as shown in FIG. 1.

A cover ring 35 is attached to the body end of the fixation ring 19 after the membrane 29 and spacer 33 are assembled to the housing 19 with the aid of the snapring 31. The cover ring 35 has an aperture at its center which is in alignment with the bore in the fixation ring housing 19 so that the central portion of the membrane 29 is exposed to the skin of the body to which the probe 1 is applied.

The plane of the membrane 29 is normally slightly recessed from the body surface of the cover ring 35 prior to attachment of the fixation ring housing 19 to the probe housing 3. However, the dimensions of the fixation ring are such that the distance from the probe end 21 to the body end 23 of the fixation ring housing 19 is slightly less than the distance of the probe housing shoulder abutted by the fixation ring probe end 21 to the body end of the probe housing 3. As a result of this relationship between the probe housing 3 and the fixation housing 19, the membrane engaging surface at the body end of the probe housing 3 extends slightly beyond the skin engaging surface at the body end of the fixation ring so that when the skin engaging surface at the body end of the cover ring 35 is held in contact with the surface of the skin, the body end of the housing 3 urges the spacer 33 and membrane 29 firmly against the skin, thereby enhancing the accuracy and precision of the measurement and obviating the possibility of relative movement between the body end of the probe 1 at which the gas sensing is accomplished and the skin. The body end of the cover ring 35 can be provided with a layer of an adhesive material 37 to adhere the probe 1 to the surface of the skin. The adhesive material 37 can be protected by a cover sheet (not shown) which has a lesser affinity for the adhesive material 37 than does the cover ring 35.

The cover ring 35, in addition to providing at its body end, a skin engaging surface for the probe 1, further aids in tensioning the membrane 29 and spacer 33 so that the membrane and spacer are drawn taut to conform to the body end of the probe 1 and are not subject to movement relative to the body end of the probe 1. Referring to FIG. 2 of the drawings it is seen that when the fixation ring housing 19 is threaded onto the probe housing 3, the body end of the probe housing 3 extends beyond a beveled membrane engaging edge 24 of the cover ring 35, which acts as a bearing surface for the membrane 29. As a result of this configuration, when the affixation ring with membrane installed is threaded onto the probe housing 3, the body end of the probe housing 3 and the body ends of the anode 5 and cathode 7 exert a force on the central portions of the spacer 33 and membrane 29 in a direction toward the body end of the probe while the cover ring 37 exerts an opposite force, that is in the probe direction, on the exterior portions of the membrane 29 and spacer 33. The opposing parallel but laterally displaced forces exerted on the membrane 29 and spacer 33 by the body end of the probe housing 3, anode 5 and cathode 7, and by the cover ring 35, respectively, cause the membrane 29 and spacer 33 to be drawn to a taut condition in which they occupy a plane substantially conforming to the planar surface defined by the body ends of the probe housing 3, anode 5 and cathode 7. The retension and stretching of the membrane 29 and spacer 33 result in a highly stable configuration obviating the need for recalibration of the probe with time and movement of the patient while the probe is attached as is often required with prior art probes.

A cap member 38 (FIG. 3) can be removably connected to the body end of the fixation ring 19 to protect the membrane 29 until it is to be applied to a patient and to prevent a buildup of ion solution adjacent the cathode 7. The cap member 38 has a flange 39 which can be snapped over the outer ridge 25 of the fixation ring housing 19. Inserted in the cap member 38 is a resilient disc 41 which, in the preferred embodiment of the invention, is made from a resilient elastic material such as a spongy foam. The distance from the flange 39 of the cap member to the resilient disc is such that when the cap member is installed on the fixation ring housing 19, the resilient disc 41 urges the membrane 29 and spacer 33 into a concave configuration when viewed from the body end of the fixation ring by pressing the center of the membrane 29 and spacer 33 toward the probe end of the fixation ring, thereby forcing the ion solution solution and any entrapped air away from the center of the probe, that is, away from the cathode 7 when the fixation ring is attached to the probe housing 3. The ion solution forced away from the center of the probe can occupy space within the probe including voids provided beneath the anode 5 and the voids provided between the lesser diameter portion of the probe housing 3 and fixation ring housing 19. The forcing of ion solution away from the center of the probe enhances measurement precision and accuracy and reduces pressure sensitivity by leaving a controlled amount of ion solution absorbed by the spacer 39 adjacent the cathode 7.

It is to be appreciated from the foregoing description that the preferred embodiment of the invention can be altered or modified without departing from the spirit and scope of the invention which is set forth in the following claims.

What is claimed is:

1. A transcutaneous gas sensor probe comprising first and second electrodes one of which is an anode and the other of which is a cathode adapted to contact an ion solution,
   a selectively permeable seal including a membrane for maintaining said solution in engagement with said electrodes and permitting said gas to permeate into said solution,
   a housing in which said electrodes are mounted having a grasping end and a body end,
   a fixation ring having a bore therethrough, a probe end and a body end, being removably attached to said housing and on which said seal is mounted including means for positively mounting said selectively permeable seal thereon
   cooperative interlocking means on said housing and on said fixation ring for positively attaching said fixation ring to said housing with said seal in engagement with said electrodes and in sealing relationship with said bore so that only matter to which said membrane is permeable can pass through said bore when said fixation ring is attached to said housing, said cooperative means preventing inadvertent relative axial movement between said electrodes and said fixation ring.

2. Apparatus according to claim 1 wherein said fixation ring has a first ridge circumscribing said bore and further comprising a ring snuggly fitted over said ridge and compressing the periphery of said membrane between said ring and said ridge.

3. Apparatus according to claim 2 further comprising a cover member mounted on the body end of said fixation ring and having an aperture in alignment with said bore, there being defined at the inner perimeter of said aperture a bearing surface for tensioning said membrane as said housing is urged against said membrane when said fixation ring is attached to said housing.

4. Apparatus according to claim 1 further comprising a cap member, having a projecting portion, removably connected to the body end of said fixation ring, said projecting portion resiliently engaging said membrane for urging said membrane into a concave configuration when viewed from the body end of said fixation ring for pressing the center of said membrane toward the grasping end of said housing thereby forcing said ion solution and any entrapped air away from the center of said housing when said fixation ring is attached to said housing.

5. Apparatus according to claim 4 wherein said projecting portion comprises a layer of a resilient material adapted to be compressed against said membrane when said cap member is attached to said fixation ring.

6. Apparatus according to claim 1 wherein said fixation ring further comprises
   means circumscribing said electrodes proximate the body ends thereof and urging said seal in an axial direction opposed to the direction in which said electrodes urge said seal for maintaining said seal taut and immovable relative to said electrodes.

7. In a transcutaneous gas probe for sensing a gas emitted through the skin of a living body including a housing having a body end and a grasping end, first and second electrodes, one of which is an anode and the other of which is a cathode, mounted in said housing, and a selectively permeable seal including a membrane impermeable to an ion forming solution and permeable to the gas to be measured for maintaining said solution in contact with said electrodes and permitting said gas to permeate therethrough and into said solution, the improvement which comprises a fixation ring having a body end, a probe end, a bore therethrough, cooperative interlocking means on said housing and on said fixation ring for positively removably attaching said housing to said fixation ring with said electrodes at least partially positioned in said bore, and means for positively mounting said membrane on said fixation ring adjacent the body end thereof, in engagement with said anode, and in sealing relationship with the bore therein, said cooperative means preventing inadvertent relative axial movement between said electrodes and said fixation ring.

8. Apparatus according to claim 7 wherein said interlocking means includes threads formed on said fixation ring, said housing having complementary threads engaging said fixation ring threads.

9. Apparatus according to claim 7 wherein said fixation ring has a ridge circumscribing one end of said bore and said mounting means includes a ring fitted over said ridge and mounted on said fixation ring with a portion of said membrane being held between said ridge and said ring.

10. Apparatus according to claim 9 wherein said ridge includes a wall which tapers radially inwardly in a direction from the body end of said fixation ring toward the probe end of said fixation ring, said ring being resiliently expandable so that it can be forced over said ridge and then contracted thereby forming a seal against said ridge.

11. Apparatus according to claim 9 further comprising a cover member having an aperture and mounted on the body end of said fixation ring with said aperture in alignment with said bore for exposing a surface of said seal.

12. Apparatus according to claim 11 wherein said cover member has one surface in engagement with said seal and another surface adapted to engage the skin of the body.

13. Apparatus according to claim 12 wherein said one surface extends inwardly of said body end of said housing and thereby exerts a force on said seal having a component in opposition to a component of the force exerted on said seal by said housing when said fixation ring is attached to said housing thereby tensioning said seal for limiting movement of said seal relative to said electrodes.

14. Apparatus according to claim 13 wherein said body end of said housing extends beyond said skin engaging surface of said cover member for urging said seal firmly against the skin when said skin engaging surface of said cover member is held in contact with the skin surface.

15. Apparatus according to claim 14 wherein said seal further comprises an absorbant spacer element mounted between said membrane and electrodes for absorbing a controlled amount of said ion solution, said spacer element being adapted to engage said first and second electrodes.

* * * * *